United States Patent
Harlan

(10) Patent No.: US 10,266,557 B2
(45) Date of Patent: Apr. 23, 2019

(54) METHOD FOR SYNTHESIS OF MONOCYCLOPENTADIENYL COMPLEXES OF ZIRCONIUM AND HAFNIUM

(71) Applicant: Univation Technologies, LLC, Houston, TX (US)

(72) Inventor: C. Jeff Harlan, Houston, TX (US)

(73) Assignee: Univation Technologies, LLC, Houston, TX (US)

(*) Notice: Subject to any disclaimer, the term of this patent is extended or adjusted under 35 U.S.C. 154(b) by 0 days.

(21) Appl. No.: 15/566,268

(22) PCT Filed: Apr. 14, 2016

(86) PCT No.: PCT/US2016/027511
§ 371 (c)(1),
(2) Date: Oct. 13, 2017

(87) PCT Pub. No.: WO2016/168448
PCT Pub. Date: Oct. 20, 2016

(65) Prior Publication Data
US 2018/0111953 A1    Apr. 26, 2018

Related U.S. Application Data

(60) Provisional application No. 62/148,913, filed on Apr. 17, 2015.

(51) Int. Cl.
*C07F 17/00* (2006.01)
*C08F 210/02* (2006.01)
(Continued)

(52) U.S. Cl.
CPC .......... *C07F 17/00* (2013.01); *C08F 4/64065* (2013.01); *C08F 4/65925* (2013.01); *C08F 210/02* (2013.01)

(58) Field of Classification Search
CPC ............... C08F 210/02; C08F 4/65925; C08F 4/64065; C07F 17/00
(Continued)

(56) References Cited

U.S. PATENT DOCUMENTS

| 3,306,919 A | 2/1967 | Brantley et al. |
| 2007/0060722 A1* | 3/2007 | Jayaratne ............... B01J 31/143 526/64 |

OTHER PUBLICATIONS

International Preliminary Report on Patentability for related PCT Application PCT/US2016/027511, dated Oct. 26, 2017 (8 pgs).
(Continued)

*Primary Examiner* — William K Cheung
(74) *Attorney, Agent, or Firm* — Brooks, Cameron & Huebsch, PLLC

(57) ABSTRACT

Catalyst systems and methods for making and using the same are disclosed. In an example, a method of synthesizing a monocyclopentadienyl compound is provided. The method includes melting a di-cyclopentadienyl compound including the following structure: (A). As used herein, M is hafnium or zirconium. Each R is independently an H, a hydrocarbyl group, a substituted hydrocarbyl group, a heteroatom group. Each X is a leaving group selected from a halogen or a heteroatom group. A reaction melt is formed by adding a metal salt including the following structure: (B). A monocyclopentadienyl compound is deposited from a vapor formed over the reaction melt, wherein the monocyclopentadienyl compound includes the following structure: (C).

20 Claims, 7 Drawing Sheets

(51) Int. Cl.
*C08F 4/64* (2006.01)
*C08F 4/6592* (2006.01)

(58) Field of Classification Search
USPC .......................................................... 526/60
See application file for complete search history.

(56) References Cited

OTHER PUBLICATIONS

International Search Report & Written Opinion for related PCT Application PCT/US2016/027511, dated Jul. 18, 2016 (13 pgs).
Darkwa, et al., "Synthetic, Structural, and Theoretical Studies on the Electron-Deficient Cubanes (RC4H4)4Ti4S4, (RC5H4)4V4S4, and [(RC5H4)4V4S4]"; Journal American Chemical Society, vol. 110, No. 1, (1988) (10 pgs).
Mach, et al., "Effects of Methyl Substituents at the Cyclopentadienyl Ligand on the Properties of C5H5TiCl3 and CH5TiAl2Ci8-x(C2H5)x (X=0-4) complexes"; Journal of Organometallic Chemistry, vol. 333 (1987) (12 pgs).

* cited by examiner

METHOD FOR SYNTHESIS OF MONOCYCLOPENTADIENYL COMPLEXES OF ZIRCONIUM AND HAFNIUM

This application is a National Stage Application under 35 U.S.C. § 371 of International Application Number PCT/US2016/027511, filed Apr. 14, 2016 and published as WO 2016/168448 on Oct. 20, 2016, which claims the benefit to U.S. Provisional Application 62/148,913, filed Apr. 17, 2015, the entire contents of which are incorporated herein by reference in its entirety.

BACKGROUND

Ethylene alpha-olefin (polyethylene) copolymers are typically produced in a low pressure reactor, utilizing, for example, solution, slurry, or gas phase polymerization processes. Polymerization takes place in the presence of catalyst systems such as those employing, for example, a Ziegler-Natta catalyst, a chromium based catalyst, a metallocene catalyst, or combinations thereof.

A number of catalyst compositions containing single site, e.g., metallocene, catalysts have been used to prepare polyethylene copolymers, producing relatively homogeneous copolymers at good polymerization rates. In contrast to traditional Ziegler-Natta catalyst compositions, single site catalyst compositions, such as metallocene catalysts, are catalytic compounds in which each catalyst molecule contains one or only a few polymerization sites. Single site catalysts often produce polyethylene copolymers that have a narrow molecular weight distribution. Control of the molecular weight distribution and other properties can be achieved through various techniques, such as using mixed ligand metallocenes.

Monocyclopentadienyl complexes of zirconium and hafnium are precursors to mixed ligand bis(cyclopentadienyl) metal complexes (mixed ligand metallocenes), such as (n-propylcyclopentadienyl) (tetramethylcyclopentadienyl) zirconiumdichloride (hereinafter catalyst A), among others.

There are several known routes to monocyclopentadienyl complexes of zirconium and hafnium. Monocyclopentadienyl complexes of zirconium and hafnium with bulky cyclopentadienyl substituents such a tetramethyl or pentamethylcyclopentadiene are relatively easy to prepare. For example, pentamethylcyclopentadienylzirconiumtrichloride can be prepared from pentamethylcyclopentadienyllithium and $ZrCl_4$ in ether.

Further, catalyst A can be made via the reaction of (tetramethyl) (trimethylsilyl) cyclopentadiene with $ZrCl_4$ at high temperature (80-90° C.) in toluene. The product precipitates out of solution and after isolation is ready for further conversion to A by treatment with n-propylcyclopentadienyllithium as shown in the following reaction scheme:

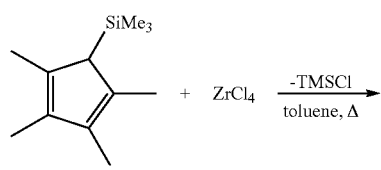

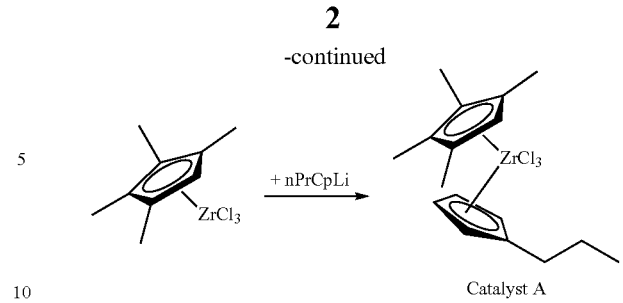

As will be discussed in more detail below, the initially formed (tetramethylcyclopentadienyl)zirconiumtrichloride is stable under these conditions and does not disproportionate to an appreciable extent as do monocyclopentadienyl complexes of zirconium and hafnium with less bulky groups such as n-propylcyclopentadienyl.

An alternative synthesis of monocyclopentadienyl complexes of zirconium and hafnium has been reported by Lund and Livinghouse in Organometallics (1990), 9(9), 2426-7. In these methods either bis(dimethylsulfide)$ZrCl_4$ or bis(dimethylsulfide)$HfCl_4$ are reacted with trimethylsilylcyclopentediene and tri-n-butyltincyclopentadiene respectively at low temperature to form the monocyclopentadienyl complexes as shown in the following reaction scheme:

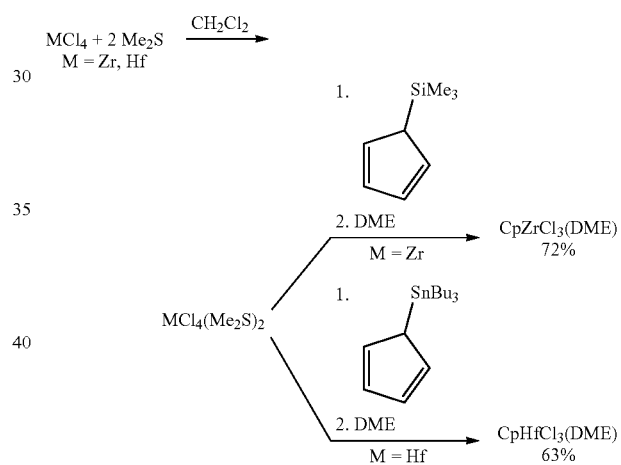

Monocyclopentadienyl complexes of zirconium and hafnium can also be formed via the reaction of metallocenes with the respective metal tetrahalide. This is especially convenient when the starting bis complex is commercially available or easily synthesized.

US2007/0060722 discloses a method for making (n-BuCp)$ZrCl_3$ from bis(n-butylcyclopentadienyl)zirconiumdichloride and zirconiumtetrachloride in which the two reactants are refuxed for 20 hours in toluene, the reaction mixture is centrifuged to remove $ZrCl_4$, and the resulting product is purified by multiple precipitations from $CH_2Cl_2$/pentane to yield the product in about 87% yield. The purity of the material is reported to have a mono to bis ratio of 52:1 as compared with the same reaction carried out at room temperature for 20 h which gave a mono to bis ratio of 1.4 to 1. There is also an example in which (1,3-butyl-methyl-cyclopentadienyl)zirconium trichloride is prepared in the same manner from bis(1,3-butyl-methylcyclopentadienyl) zirconiumdichloride (E dichloride) and $ZrCl_4$ in 76% yield.

The procedures detailed above may provide a monocyclopentadienyl complex, but take significant time for completion. Further, in many of these techniques only bulky substituents on the cyclopentadiene ring slow or prevent disproportionation to a dicyclopentadienyl complex.

SUMMARY

Figure 1:
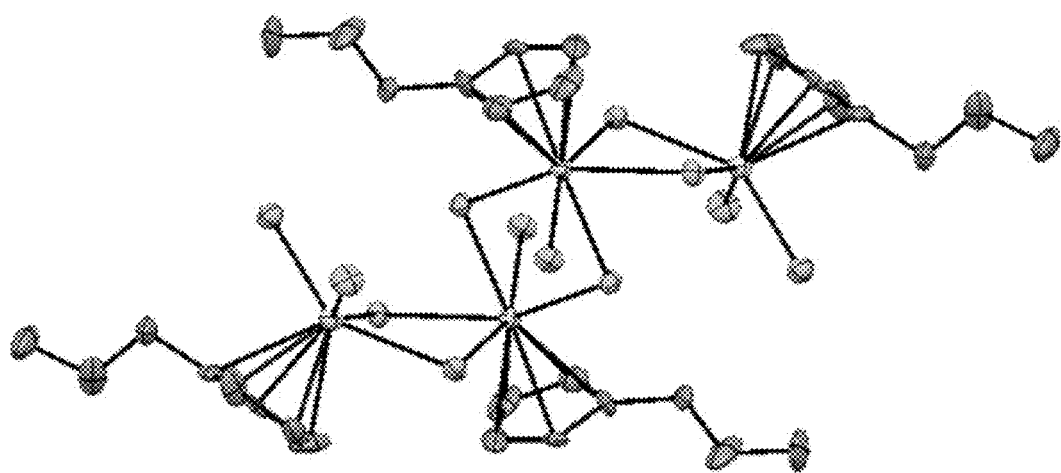
FIG. 1 is a drawing of a structure for (n-propylcyclopentadienyl) zirconiumtrichloride.

An example described herein provides a method of synthesizing a catalyst compound is provided. The method includes melting a dicyclopentadienyl compound including the following structure:

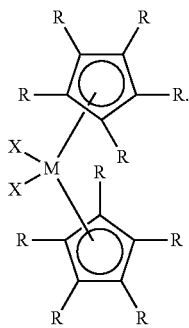

As used herein, M is hafnium or zirconium. Each R is independently an H, a hydrocarbyl group, a substituted hydrocarbyl group, a heteroatom group. Each X is a leaving group selected from a halogen or a heteroatom group. A reaction melt is formed by adding a metal salt including the following structure:

A monocyclopentadienyl compound is deposited from a vapor formed over the reaction melt, wherein the monocyclopentadienyl compound includes the following structure:

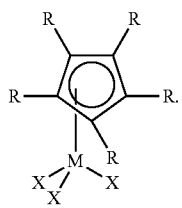

The monocyclopentadienyl compound is reacted with a ligand precursor to form the catalyst compound.

Another example described herein provides a method of forming a polyethylene copolymer. The method includes reacting ethylene and a $C_4$-$C_{20}$ alpha-olefin with a polymerization catalyst, wherein the polymerization catalyst is formed by synthesizing a monocyclopentadienyl compound by melting a dicyclopentadienyl compound including the following structure:

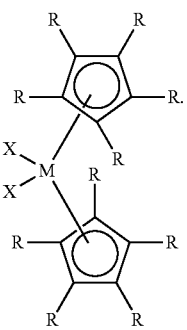

As used herein, M is hafnium or zirconium. Each R is independently an H, a hydrocarbyl group, a substituted hydrocarbyl group, a heteroatom group. Each X is a leaving group selected from a halogen or a heteroatom group. A reaction melt is formed by adding a metal salt including the following structure:

A monocyclopentadienyl compound is deposited from a vapor formed over the reaction melt, wherein the monocyclopentadienyl compound includes the following structure:

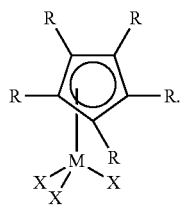

The monocyclopentadienyl compound is reacted with a ligand precursor to form the catalyst compound. The catalyst compound is supported to form the polymerization catalyst.

Another example described herein provides a method of forming a monocyclopentadienyl complex of hafnium or zirconium. The method includes melting a dicyclopentadienyl compound including the following structure:

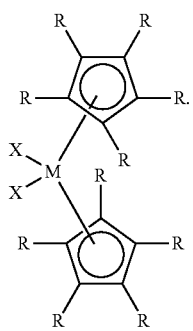

As used herein, M is hafnium or zirconium. Each R is independently an H, a hydrocarbyl group, a substituted hydrocarbyl group, a heteroatom group. Each X is a leaving group selected from a halogen or a heteroatom group. A reaction melt is formed by adding a metal salt including the following structure:

A monocyclopentadienyl compound is deposited from a vapor formed over the reaction melt, wherein the monocyclopentadienyl compound includes the following structure:

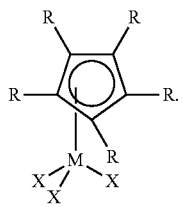

DETAILED DESCRIPTION

Examples described herein provide a method for forming a monocyclopentadienyl species. The method include reacting a bis(cyclopentadienyl)zirconium or hafnium species with $ZrCl_4$ or $HfCl_4$, wherein the reaction is driven to completion via sublimation or distillation of the product monocyclopentadienyl species out of the reaction mixture. As an example, the reaction procedure takes advantage of the equilibrium shown in equation 1:

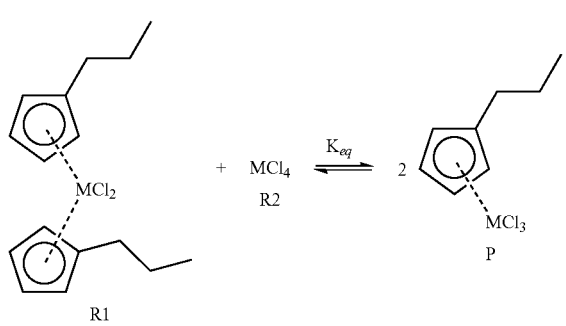

(1)

In equation 1, M can be either zirconium (Zr) or hafnium (Hf). The equilibrium constant, $K_{eq}$, depends on the metal (Zr vs Hf) and the steric hindrance or size of cyclopentadienyl ligand. The equilibrium may lie farther to the right for Hf than for Zr and it may also lie farther to the right the larger the cyclopentadienyl ligand. The reactants, R1 and R2, are melted together in an inert atmosphere to form a reaction melt. The product (P) forms in the reaction melt and is sublimed or distilled from the reaction melt, driving the reaction to the right. The product is then deposited in a cooler region of an apparatus. The sublimed or distilled product typically has a purity of >95% and can be purified further, for example, by precipitation as the DME adduct in toluene.

The technique may be used in commercial processes to form the product continuously. This would be performed by continuously adding the dicyclopentadienyl compound and the metal salt to the reaction melt, while continuously depositing the monocyclopentadienyl compound from the vapor.

Catalyst Compounds

Metallocene Catalyst Compounds

Metallocene catalyst compounds can include "half sandwich" and/or "full sandwich" compounds having one or more Cp ligands (cyclopentadienyl and ligands isolobal to cyclopentadienyl) bound to at least one Group 3 to Group 12 metal atom, and one or more leaving groups bound to the at least one metal atom. As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced there with permission from IUPAC), unless reference is made to the Previous IUPAC form noted with Roman numerals (also appearing in the same), or unless otherwise noted.

The Cp ligands are one or more rings or ring systems, at least a portion of which includes π-bonded systems, such as cycloalkadienyl ligands and heterocyclic analogues. The rings or ring systems typically include atoms selected from the group consisting of Groups 13 to 16 atoms, and, in a particular example, the atoms that make up the Cp ligands are selected from the group consisting of carbon, nitrogen, oxygen, silicon, sulfur, phosphorous, germanium, boron, aluminum, and combinations thereof, where carbon makes up at least 50% of the ring members. In a more particular example, the Cp ligands are selected from the group consisting of substituted and unsubstituted cyclopentadienyl ligands and ligands isolobal to cyclopentadienyl, non-limiting examples of which include cyclopentadienyl, indenyl, fluorenyl and other structures. Further non-limiting examples of such ligands include cyclopentadienyl, cyclopentaphenanthreneyl, indenyl, benzindenyl, fluorenyl, octahydrofluorenyl, cyclooctatetraenyl, cyclopentacyclododecene, phenanthrindenyl, 3,4-benzofluorenyl, 9-phenylfluorenyl, 8-H-cyclopent[a]acenaphthylenyl, 7-H-dibenzofluorenyl, indeno[1,2-9]anthrene, thiophenoindenyl, thiophenofluorenyl, hydrogenated versions thereof (e.g., 4,5, 6,7-tetrahydroindenyl, or "$H_4$ Ind"), substituted versions thereof (as discussed and described in more detail below), and heterocyclic versions thereof.

The metal atom "M" of the metallocene catalyst compound can be selected from the group consisting of Groups 3 through 12 atoms and lanthanide Group atoms in one example; and selected from the group consisting of Groups 3 through 10 atoms in a more particular example, and selected from the group consisting of Sc, Ti, Zr, Hf, V, Nb, Ta, Mn, Re, Fe, Ru, Os, Co, Rh, Ir, and Ni in a more particular example; and selected from the group consisting of Groups 4, 5, and 6 atoms in a more particular example, and Ti, Zr, Hf atoms in a more particular example, and Hf in a more particular example. The oxidation state of the metal atom "M" can range from 0 to +7 in one example; and in a more particular example, can be +1, +2, +3, +4, or +5; and in a more particular example can be +2, +3 or +4. The groups bound to the metal atom "M" are such that the compounds described below in the formulas and structures are electrically neutral, unless otherwise indicated. The Cp ligand forms at least one chemical bond with the metal atom M to form the "metallocene catalyst compound." The Cp ligands are distinct from the leaving groups bound to the catalyst compound in that they are not highly susceptible to substitution/abstraction reactions.

The one or more metallocene catalyst compounds can be represented by the formula (I):

$$Cp^A Cp^B MX_n \qquad (I)$$

in which M is as described above; each X is chemically bonded to M; each Cp group is chemically bonded to M; and n is 0 or an integer from 1 to 4, and either 1 or 2 in a particular example.

The ligands represented by $Cp^A$ and $Cp^B$ in formula (I) can be the same or different cyclopentadienyl ligands or ligands isolobal to cyclopentadienyl, either or both of which can contain heteroatoms and either or both of which can be substituted by a group R. In at least one specific example, $Cp^A$ and $Cp^B$ are independently selected from the group consisting of cyclopentadienyl, indenyl, tetrahydroindenyl, fluorenyl, and substituted derivatives of each.

Independently, each $Cp^A$ and $Cp^B$ of formula (I) can be unsubstituted or substituted with any one or combination of substituent groups R. Non-limiting examples of substituent groups R as used in structure (I) as well as ring substituents in structures Va-d, discussed and described below, include groups selected from the group consisting of hydrogen radicals, alkyls, alkenyls, alkynyls, cycloalkyls, aryls, acyls, aroyls, alkoxys, aryloxys, alkylthiols, dialkylamines, alkylamidos, alkoxycarbonyls, aryloxycarbonyls, carbamoyls, alkyl- and dialkyl-carbamoyls, acyloxys, acylaminos, aroylaminos, and combinations thereof. More particular non-limiting examples of alkyl substituents R associated with formulas (I) through (Va-d) include methyl, ethyl, propyl, butyl, pentyl, hexyl, cyclopentyl, cyclohexyl, benzyl, phenyl, methylphenyl, and tert-butylphenyl groups and the like, including all their isomers, for example, tertiary-butyl, isopropyl, and the like. Other possible radicals include substituted alkyls and aryls such as, for example, fluoromethyl, fluroethyl, difluroethyl, iodopropyl, bromohexyl, chlorobenzyl, hydrocarbyl substituted organometalloid radicals including trimethylsilyl, trimethylgermyl, methyldiethylsilyl, and the like, and halocarbyl-substituted organometalloid radicals, including tris(trifluoromethyl)silyl, methylbis(difluoromethyl)silyl, bromomethyldimethylgermyl and the like; and disubstituted boron radicals including dimethylboron, for example; and disubstituted Group 15 radicals including dimethylamine, dimethylphosphine, diphenylamine, methylphenylphosphine, as well as Group 16 radicals including methoxy, ethoxy, propoxy, phenoxy, methylsulfide, and ethylsulfide. Other substituent groups R include, but are not limited to, olefins such as olefinically unsaturated substituents including vinyl-terminated ligands such as, for example, 3-butenyl, 2-propenyl, 5-hexenyl, and the like. In one example, at least two R groups (two adjacent R groups in a particular example) are joined to form a ring structure having from 3 to 30 atoms selected from the group consisting of carbon, nitrogen, oxygen, phosphorous, silicon, germanium, aluminum, boron, and combinations thereof. Also, a substituent group R such as 1-butanyl can form a bonding association to the element M.

Each X in the formula (I) above and for the formulas, or structures, (II) through (Va-d) below is independently selected from the group consisting of: any leaving group, in one example; halogen ions, hydrides, $C_1$ to $C_{12}$ alkyls, $C_2$ to $C_{12}$ alkenyls, $C_6$ to $C_{12}$ aryls, $C_7$ to $C_{20}$ alkylaryls, $C_1$ to $C_{12}$ alkoxys, $C_6$ to $C_{16}$ aryloxys, $C_7$ to $C_8$ alkylaryloxys, $C_1$ to $C_{12}$ fluoroalkyls, $C_6$ to $C_{12}$ fluoroaryls, and $C_1$ to $C_{12}$ heteroatom-containing hydrocarbons and substituted derivatives thereof, in a more particular example; hydride, halogen ions, $C_1$ to $C_6$ alkyls, $C_2$ to $C_6$ alkenyls, $C_7$ to $C_{18}$ alkylaryls, $C_1$ to $C_6$ alkoxys, $C_6$ to $C_{14}$ aryloxys, $C_7$ to $C_{16}$ alkylaryloxys, $C_1$ to $C_6$ alkylcarboxylates, $C_1$ to $C_6$ fluorinated alkylcarboxylates, $C_6$ to $C_{12}$ arylcarboxylates, $C_7$ to $C_{18}$ alkylarylcarboxylates, $C_1$ to $C_6$ fluoroalkyls, $C_2$ to $C_6$ fluoroalkenyls, and $C_7$ to $C_{18}$ fluoroalkylaryls in a more particular example; hydride, chloride, fluoride, methyl, phenyl, phenoxy, benzoxy, tosyl, fluoromethyls and fluorophenyls, in a more particular example; $C_1$ to $C_{12}$ alkyls, $C_2$ to $C_{12}$ alkenyls, $C_6$ to $C_{12}$ aryls, $C_7$ to $C_{20}$ alkylaryls, substituted $C_1$ to $C_{12}$ alkyls, substituted $C_6$ to $C_{12}$ aryls, substituted $C_7$ to $C_{20}$ alkylaryls and $C_1$ to $C_{12}$ heteroatom-containing alkyls, $C_1$ to $C_{12}$ heteroatom-containing aryls, and $C_1$ to $C_{12}$ heteroatom-containing alkylaryls, in a more particular example; chloride, fluoride, $C_1$ to $C_6$ alkyls, $C_2$ to $C_6$ alkenyls, $C_7$ to $C_{18}$ alkylaryls, halogenated $C_1$ to $C_6$ alkyls, halogenated $C_2$ to $C_6$ alkenyls, and halogenated $C_7$ to $C_{18}$ alkylaryls, in a more particular example; fluoride, methyl, ethyl, propyl, phenyl, methylphenyl, dimethylphenyl, trimethylphenyl, fluoromethyls (mono-, di- and trifluoromethyls) and fluorophenyls (mono-, di-, tri-, tetra- and pentafluorophenyls), in a more particular example; and fluoride, in a more particular example.

Other non-limiting examples of X groups include amines, phosphines, ethers, carboxylates, dienes, hydrocarbon radicals having from 1 to 20 carbon atoms, fluorinated hydrocarbon radicals (e.g., $-C_6F_5$ (pentafluorophenyl)), fluorinated alkylcarboxylates (e.g., $CF_3C(O)O^-$), hydrides, halogen ions and combinations thereof. Other examples of X ligands include alkyl groups such as cyclobutyl, cyclohexyl, methyl, heptyl, tolyl, trifluoromethyl, tetramethylene, pentamethylene, methylidene, methyoxy, ethyoxy, propoxy, phenoxy, bis(N-methylanilide), dimethylamide, dimethylphosphide radicals and the like. In one example, two or more Xs form a part of a fused ring or ring system. In at least one specific example, X can be a leaving group selected from the group consisting of chloride ions, bromide ions, $C_1$ to $C_{10}$ alkyls, and $C_2$ to $C_{12}$ alkenyls, carboxylates, acetylacetonates, and alkoxides.

The catalyst system can include other single site catalysts such as Group 15-containing catalysts. The catalyst system can include one or more second catalysts in addition to the single site catalyst compound such as chromium-based catalysts, Ziegler-Natta catalysts, one or more additional single-site catalysts such as metallocenes or Group 15-containing catalysts, bimetallic catalysts, and mixed catalysts. The catalyst system can also include $AlCl_3$, cobalt, iron, palladium, or any combination thereof.

Catalyst Slurry

The catalyst system may include a catalyst or catalyst component in a slurry, which may have a single catalyst compound, or may have added catalyst components that are added as a solution to the slurry or cosupported on the support. Any number of combinations of catalyst components may be used in examples. For example, the catalyst component slurry can include an activator and a support, or a supported activator. Further, the slurry can include a catalyst compound in addition to the activator and the support. As noted, the catalyst compound in the slurry may be supported.

The slurry may include one or more activators and supports, and one more catalyst compounds. For example, the slurry may include two or more activators (such as alumoxane and a modified alumoxane) and a catalyst compound, or the slurry may include a supported activator and more than one catalyst compounds. In one example, the slurry includes a support, an activator, and a catalyst compound. In another example the slurry includes a support, an activator and two different catalyst compounds, which may be added to the slurry separately or in combination. The slurry, containing silica and alumoxane, may be contacted with a catalyst compound, allowed to react, and thereafter the slurry is contacted with another catalyst compound, for example, in a trim system.

The molar ratio of metal in the activator to metal, such as aluminum, or metalloid, such as boron, in the catalyst compound in the slurry may be 1000:1 to 0.5:1, 300:1 to 1:1, or 150:1 to 1:1. The slurry can include a support material which may be any inert particulate carrier material known in the art, including, but not limited to, silica, fumed silica, alumina, clay, talc or other support materials such as disclosed above. In one example, the slurry contains silica and an activator, such as methyl aluminoxane ("MAO"), modified methyl aluminoxane ("MMAO"), as discussed further below.

One or more diluents or carriers can be used to facilitate the combination of any two or more components of the catalyst system in the slurry or in the trim catalyst solution. For example, the single site catalyst compound and the activator can be combined together in the presence of toluene or another non-reactive hydrocarbon or hydrocarbon mixture to provide the catalyst mixture. In addition to toluene, other suitable diluents can include, but are not limited to, ethylbenzene, xylene, pentane, hexane, heptane, octane, other hydrocarbons, or any combination thereof. The support, either dry or mixed with toluene can then be added to the catalyst mixture or the catalyst/activator mixture can be added to the support.

Catalyst Supports

As used herein, the terms "support" and "carrier" are used interchangeably and refer to any support material, including a porous support material, such as talc, inorganic oxides, and inorganic chlorides. The one or more single site catalyst compounds of the slurry can be supported on the same or separate supports together with the activator, or the activator can be used in an unsupported form, or can be deposited on a support different from the single site catalyst compounds, or any combination thereof. This may be accomplished by any technique commonly used in the art. There are various other methods in the art for supporting a single site catalyst compound. For example, the single site catalyst compound can contain a polymer bound ligand. The single site catalyst compounds of the slurry can be spray dried. The support used with the single site catalyst compound can be functionalized.

The support can be or include one or more inorganic oxides, for example, of Group 2, 3, 4, 5, 13, or 14 elements. The inorganic oxide can include, but is not limited to silica, alumina, titania, zirconia, boria, zinc oxide, magnesia, or any combination thereof. Illustrative combinations of inorganic oxides can include, but are not limited to, alumina-silica, silica-titania, alumina-silica-titania, alumina-zirconia, alumina-titania, and the like. The support can be or include alumina, silica, or a combination thereof. In one example described herein, the support is silica.

Suitable commercially available silica supports can include, but are not limited to, ES757, ES70, and ES70W available from PQ Corporation. Suitable commercially available silica-alumina supports can include, but are not limited to, SIRAL® 1, SIRAL® 5, SIRAL® 10, SIRAL® 20, SIRAL® 28M, SIRAL® 30, and SIRAL® 40, available from SASOL®. Generally, catalysts supports comprising silica gels with activators, such as methylaluminoxanes (MAOs), are used in the trim systems described, since these supports may function better for co-supporting solution carried catalysts. Suitable supports may also be selected from the Cab-o-Sil® materials available from Cabot Corporation and silica materials available from the Grace division of W.R. Grace & Company.

Catalyst supports may also include polymers that are covalently bonded to a ligand on the catalyst. For example, two or more catalyst molecules may be bonded to a single polyolefin chain.

Catalyst Activators

As used herein, the term "activator" may refer to any compound or combination of compounds, supported, or unsupported, which can activate a single site catalyst compound or component, such as by creating a cationic species of the catalyst component. For example, this can include the abstraction of at least one leaving group (the "X" group in the single site catalyst compounds described herein) from the metal center of the single site catalyst compound or component. The activator may also be referred to as a "co-catalyst".

For example, the activator can include a Lewis acid or a non-coordinating ionic activator or ionizing activator, or any other compound including Lewis bases, aluminum alkyls, and/or conventional-type co-catalysts. In addition to methylaluminoxane ("MAO") and modified methylaluminoxane ("MMAO") mentioned above, illustrative activators can include, but are not limited to, aluminoxane or modified aluminoxane, and/or ionizing compounds, neutral or ionic, such as Dimethylanilinium tetrakis(pentafluorophenyl)borate, Triphenylcarbenium tetrakis(pentafluorophenyl)borate, Dimethylanilinium tetrakis(3,5-$(CF_3)_2$phenyl)borate, Triphenylcarbenium tetrakis(3,5-$(CF_3)_2$phenyl)borate, Dimethylanilinium tetrakis(perfluoronapthyl)borate, Triphenylcarbenium tetrakis(perfluoronapthyl)borate, Dimethylanilinium tetrakis(pentafluorophenyl)aluminate, Triphenylcarbenium tetrakis(pentafluorophenyl)aluminate, Dimethylanilinium tetrakis(perfluoronapthyl)aluminate, Triphenylcarbenium tetrakis(perfluoronapthyl)aluminate, a tris(perfluorophenyl)boron, a tris(perfluoronaphthyl)boron, tris(perfluorophenyl)aluminum, a tris(perfluoronaphthyl)aluminum or any combinations thereof.

It is recognized that these activators may bind directly to the support surface or be modified to allow them to be bound to a support surface while still maintaining their compatibility with the polymerization system. Such tethering agents may be derived from groups that are reactive with surface hydroxyl species. Non-limiting examples of reactive functional groups that can be used to create tethers include aluminum halides, aluminum hydrides, aluminum alkyls, aluminum aryls, sluminum alkoxides, electrophilic silicon reagents, alkoxy silanes, amino silanes, boranes.

Aluminoxanes can be described as oligomeric aluminum compounds having —Al(R)—O— subunits, where R is an alkyl group. Examples of aluminoxanes include, but are not limited to, methylaluminoxane ("MAO"), modified methylaluminoxane ("MMAO"), ethylaluminoxane, isobutylaluminoxane, or a combination thereof. Aluminoxanes can be produced by the hydrolysis of the respective trialkylaluminum compound. MMAO can be produced by the hydrolysis of trimethylaluminum and a higher trialkylaluminum, such as triisobutylaluminum. MMAOs are generally more soluble in aliphatic solvents and more stable during storage. There are a variety of methods for preparing aluminoxane and modified aluminoxanes.

In one or more examples, a visually clear MAO can be used. For example, a cloudy or gelled aluminoxane can be filtered to produce a clear aluminoxane or clear aluminoxane can be decanted from a cloudy aluminoxane solution. In another example, a cloudy and/or gelled aluminoxane can be used. Another aluminoxane can include a modified methyl aluminoxane ("MMAO") type 3A (commercially available from Akzo Chemicals, Inc. under the trade name Modified Methylaluminoxane type 3A, discussed and described in U.S. Pat. No. 5,041,584). A suitable source of MAO can be a solution having from about 1 wt. % to about a 50 wt. % MAO, for example. Commercially available MAO solutions can include the 10 wt. % and 30 wt. % MAO solutions available from Albemarle Corporation, of Baton Rouge, La.

As noted above, one or more organo-aluminum compounds such as one or more alkylaluminum compounds can be used in conjunction with the aluminoxanes. For example, alkylaluminum species that may be used are diethylaluminum ethoxide, diethylaluminum chloride, and/or diisobutylaluminum hydride. Examples of trialkylaluminum compounds include, but are not limited to, trimethylaluminum, triethylaluminum ("TEAL"), triisobutylaluminum ("TiBAl"), tri-n-hexylaluminum, tri-n-octylaluminum, tripropylaluminum, tributylaluminum, and the like.

Continuity Additive/Static Control Agents

In gas-phase polyethylene production processes, as disclosed herein, it may be desirable to additionally use one or more static control agents to aid in regulating static levels in the reactor. As used herein, a static control agent is a chemical composition which, when introduced into a fluidized bed reactor, may influence or drive the static charge (negatively, positively, or to zero) in the fluidized bed. The specific static control agent used may depend upon the nature of the static charge, and the choice of static control agent may vary dependent upon the polymer being produced and the single site catalyst compounds being used.

Control agents such as aluminum stearate may be employed. The static control agent used may be selected for its ability to receive the static charge in the fluidized bed without adversely affecting productivity. Other suitable static control agents may also include aluminum distearate, ethoxlated amines, and anti-static compositions such as those provided by Innospec Inc. under the trade name OCTASTAT. For example, OCTASTAT 2000 is a mixture of a polysulfone copolymer, a polymeric polyamine, and oil-soluble sulfonic acid.

Any of the aforementioned control agents, as well as those described in, for example, WO 01/44322, listed under the heading Carboxylate Metal Salt and including those chemicals and compositions listed as antistatic agents may be employed either alone or in combination as a control agent. For example, the carboxylate metal salt may be combined with an amine containing control agent (e.g., a carboxylate metal salt with any family member belonging to the KEMA-MINE® (available from Crompton Corporation) or ATMER® (available from ICI Americas Inc.) family of products).

Other useful continuity additives include ethyleneimine additives useful in examples disclosed herein may include polyethyleneimines having the following general formula:

in which n may be from about 10 to about 10,000. The polyethyleneimines may be linear, branched, or hyper-branched (e.g., forming dendritic or arborescent polymer structures). They can be a homopolymer or copolymer of ethyleneimine or mixtures thereof (referred to as polyethyleneimine(s) hereafter). Although linear polymers represented by the chemical formula —[CH$_2$—CH$_2$—NH]— may be used as the polyethyleneimine, materials having primary, secondary, and tertiary branches can also be used. Commercial polyethyleneimine can be a compound having branches of the ethyleneimine polymer. Suitable polyethyleneimines are commercially available from BASF Corporation under the trade name Lupasol. These compounds can be prepared as a wide range of molecular weights and product activities. Examples of commercial polyethyleneimines sold by BASF suitable for use in the present invention include, but are not limited to, Lupasol FG and Lupasol WF. Another useful continuity additive can include a mixture of aluminum distearate and an ethoxylated amine-type compound, e.g., IRGASTAT AS-990, available from Huntsman (formerly Ciba Specialty Chemicals). The mixture of aluminum distearate and ethoxylated amine type compound can be slurried in mineral oil e.g., Hydrobrite 380. For example, the mixture of aluminum distearate and an ethoxylated amine type compound can be slurried in mineral oil to have total slurry concentration of ranging from about 5 wt. % to about 50 wt. % or about 10 wt. % to about 40 wt. %, or about 15 wt. % to about 30 wt. %.

The continuity additive(s) or static control agent(s) may be added to the reactor in an amount ranging from 0.05 to 200 ppm, based on the weight of all feeds to the reactor, excluding recycle. In some examples, the continuity additive may be added in an amount ranging from 2 to 100 ppm, or in an amount ranging from 4 to 50 ppm.

Polymerization Process

The catalyst system can be used to polymerize one or more olefins to provide one or more polymer products therefrom. Any suitable polymerization process can be used, including, but not limited to, high pressure, solution, slurry, and/or gas phase polymerization processes.

The terms "polyethylene" and "polyethylene copolymer" refer to a polymer having at least 50 wt. % ethylene-derived units. In various examples, the polyethylene can have at least 70 wt. % ethylene-derived units, at least 80 wt. % ethylene-derived units, at least 90 wt. % ethylene-derived units, at least 95 wt. % ethylene-derived units, or 100 wt. % ethylene-derived units. The polyethylene can, thus, be a homopolymer or a copolymer, including a terpolymer, having one or more other monomeric units. As described herein, a polyethylene can include, for example, at least one or more other olefins or comonomers. Suitable comonomers can contain 3 to 16 carbon atoms, from 3 to 12 carbon atoms, from 4 to 10 carbon atoms, and from 4 to 8 carbon atoms. Examples of comonomers include, but are not limited to, propylene, 1-butene, 1-pentene, 1-hexene, 1-heptene, 1-octene, 4-methylpent-1-ene, 1-decene, 1-dodecene, 1-hexadecene, and the like. Additionally, small amounts of diene monomers, such as 1,7-octadiene may be added to the polymerization to adjust polymer properties.

The reactor temperature of a fluid bed in a gas phase polymerization process can be greater than about 30° C., about 40° C., about 50° C., about 90° C., about 100° C., about 110° C., about 120° C., about 150° C., or higher. In general, the reactor temperature is operated at the highest feasible temperature taking into account the sintering temperature of the polymer product within the reactor. Preferred reactor temperatures are between 70 and 95° C. More preferred reactor temperatures are between 75 and 90° C. Thus, the upper temperature limit in one example is the melting temperature of the polyethylene copolymer produced in the reactor. However, higher temperatures may result in narrower MWDs, which can be improved by the addition of the MCN, or other, co-catalysts, as described herein.

Hydrogen gas can be used in olefin polymerization to control the final properties of the polyolefin. Using certain catalyst systems, increasing concentrations (partial pressures) of hydrogen can increase the flow index (FI) of the polyethylene copolymer generated. The flow index can thus be influenced by the hydrogen concentration. The amount of hydrogen in the polymerization can be expressed as a mole ratio relative to the total polymerizable monomer, for example, ethylene, or a blend of ethylene and hexene or propylene.

The amount of hydrogen used in the polymerization process can be an amount necessary to achieve the desired flow index of the final polyolefin resin. For example, the mole ratio of hydrogen to total monomer ($H_2$:monomer) can be greater than about 0.0001, greater than about 0.0005, or greater than about 0.001. Further, the mole ratio of hydrogen to total monomer ($H_2$:monomer) can be less than about 10, less than about 5, less than about 3, and less than about 0.10. A desirable range for the mole ratio of hydrogen to monomer can include any combination of any upper mole ratio limit with any lower mole ratio limit described herein. Expressed another way, the amount of hydrogen in the reactor at any time can range to up to about 5,000 ppm, up to about 4,000 ppm in another example, up to about 3,000 ppm, or between about 50 ppm and 5,000 ppm, or between about 50 ppm and 2,000 ppm in another example. The amount of hydrogen in the reactor can range from a low of about 1 ppm, about 50 ppm, or about 100 ppm to a high of about 400 ppm, about 800 ppm, about 1,000 ppm, about 1,500 ppm, or about 2,000 ppm. Further, the ratio of hydrogen to total monomer ($H_2$:monomer) can be about 0.00001:1 to about 2:1, about 0.005:1 to about 1.5:1, or about 0.0001:1 to about 1:1. The one or more reactor pressures in a gas phase process (either single stage or two or more stages) can vary from 690 kPa (100 psig) to 3,448 kPa (500 psig), in the range from 1,379 kPa (200 psig) to 2,759 kPa (400 psig), or in the range from 1,724 kPa (250 psig) to 2,414 kPa (350 psig).

The gas phase reactor can be capable of producing from about 10 kg of polymer per hour (25 lbs/hr) to about 90,900 kg/hr (200,000 lbs/hr), or greater, and greater than about 455 kg/hr (1,000 lbs/hr), greater than about 4,540 kg/hr (10,000 lbs/hr), greater than about 11,300 kg/hr (25,000 lbs/hr), greater than about 15,900 kg/hr (35,000 lbs/hr), and greater than about 22,700 kg/hr (50,000 lbs/hr), and from about 29,000 kg/hr (65,000 lbs/hr) to about 45,500 kg/hr (100,000 lbs/hr).

As noted, a slurry polymerization process can also be used in examples. A slurry polymerization process generally uses pressures in the range of from about 101 kPa (1 atmosphere) to about 5,070 kPa (50 atmospheres) or greater, and temperatures in the range of from about 0° C. to about 120° C., and more particularly from about 30° C. to about 100° C. In a slurry polymerization, a suspension of solid, particulate polymer can be formed in a liquid polymerization diluent medium to which ethylene, comonomers, and hydrogen along with catalyst can be added. The suspension including diluent can be intermittently or continuously removed from the reactor where the volatile components are separated from the polymer and recycled, optionally after a distillation, to the reactor. The liquid diluent employed in the polymerization medium can be an alkane having from 3 to 7 carbon atoms, such as, for example, a branched alkane. The medium employed should be liquid under the conditions of polymerization and relatively inert. When a propane medium is used the process should be operated above the reaction diluent critical temperature and pressure. In one example, a hexane, isopentane, or isobutane medium can be employed. The slurry can be circulated in a continuous loop system.

The product polyethylene can have a melt index ratio (MIR or $I_{21}/I_2$) ranging from about 5 to about 300, or from about 10 to less than about 150, or, in many examples, from about 15 to about 50. Flow index (FI, HLMI, or $I_{21}$ can be measured in accordance with ASTM D1238 (190° C., 21.6 kg). The melt index (MI, $I_2$) can be measured in accordance with ASTM D1238 (at 190° C., 2.16 kg weight).

Density can be determined in accordance with ASTM D-792. Density is expressed as grams per cubic centimeter (g/cm$^3$) unless otherwise noted. The polyethylene can have a density ranging from a low of about 0.89 g/cm$^3$, about 0.90 g/cm$^3$, or about 0.91 g/cm$^3$ to a high of about 0.95 g/cm$^3$, about 0.96 g/cm$^3$, or about 0.97 g/cm$^3$. The polyethylene can have a bulk density, measured in accordance with ASTM D1895 method B, of from about 0.25 g/cm$^3$ to about 0.5 g/cm$^3$. For example, the bulk density of the polyethylene can range from a low of about 0.30 g/cm$^3$, about 0.32 g/cm$^3$, or about 0.33 g/cm$^3$ to a high of about 0.40 g/cm$^3$, about 0.44 g/cm$^3$, or about 0.48 g/cm$^3$.

Controlling Product Properties

The properties of the product polymer may be controlled by adjusting the timing, temperature, concentrations, and sequence of the mixing of the solution, the slurry and any optional added materials (nucleating agents, catalyst compounds, activators, etc.) described above. The control may be achieved by measuring a sample of the polyethylene copolymer to obtain an initial product property; and changing a process parameter to obtain a second product property, based, at least in part, on the initial product property.

The MWD, composition distribution, melt index, relative amount of polymer produced by each catalyst, and other properties of the polymer produced may also be changed by manipulating process parameters. Any number of process parameters may be adjusted, including manipulating hydrogen concentration in the polymerization system, changing the amount of a catalyst in the polymerization system, changing the amount of a second catalyst in the polymerization system. Other process parameters that can be adjusted include changing the relative ratio of the catalyst in the polymerization process, and optionally adjusting their individual feed rates to maintain a steady or constant resin production rate. The concentrations of reactants in the reactor can be adjusted by changing the amount of liquid or gas that is withdrawn or purged from the process, changing the amount and/or composition of a recovered liquid and/or recovered gas returned to the polymerization process, wherein the recovered liquid or recovered gas can be recovered from polymer discharged from the polymerization process. Further concentration parameters that can be adjusted include changing the polymerization temperature, changing the ethylene partial pressure in the polymerization process, changing the ethylene to comonomer ratio in the polymerization process, changing the activator to transition metal ratio in the activation sequence. Time dependent parameters may be adjusted, such as changing the relative feed rates of the slurry or solution, changing the mixing time, the temperature and or degree of mixing of the slurry and the solution in-line, adding different types of activator compounds to the polymerization process, and adding oxygen or fluorobenzene or other catalyst poison to the polymerization process. Any combinations of these adjustments may be used to control the properties of the final polymer product.

In one example, the composition distribution of the polymer product is measured at regular intervals and one of the above process parameters, such as temperature, catalyst compound feed rate, the ratio of comonomer to monomer, the monomer partial pressure, and or hydrogen concentration, is altered to bring the composition to the desired level, if necessary. The composition distribution may be performed by temperature rising elution fractionation (TREF), or similar techniques.

The polyethylene can be suitable for such articles as films, fibers, nonwoven and/or woven fabrics, extruded articles, and/or molded articles. Examples of films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications, agricultural films and sheets. Examples of fibers include melt spinning, solution spinning and melt blown fiber operations for use in woven or nonwoven form to make filters, diaper fabrics, hygiene products, medical garments, geotextiles, etc. Examples of extruded articles include tubing, medical tubing, wire and cable coatings, pipe, geomembranes, and pond liners. Examples of molded articles include single and multi-layered constructions in the form of bottles, tanks, large hollow articles, rigid food containers and toys, etc.

EXAMPLES

To provide a better understanding of the foregoing discussion, the following non-limiting examples are provided. All parts, proportions, and percentages are by weight unless otherwise indicated.

General Experimental Procedures

All manipulations were performed in an $N_2$ purged glovebox or using standard Schlenk techniques. All anhydrous solvents were purchased from Sigma-Aldrich and were degassed and dried over calcined $Al_2O_3$ beads or molecular sieves prior to use. Deuterated solvents were purchased from Cambridge Isotope Laboratories and were degassed and dried over alumina beads or molecular sieves prior to use. Reagents used were purchased from various commercial suppliers or made by literature methods. $^1$H NMR measurements were recorded on a 250 MHz, 400 MHz or a 500 MHz Bruker spectrometer.

Catalyst Preparations

Synthesis of
(n-propylcyclopentadienyl)zirconiumtrichloride

Bis(n-propylcyclopentadienyl)zirconiumdichloride (14.83 g) was heated to 130° C. with stirring forming a viscous liquid. $ZrCl_4$ (9.18 g) was added. The temperature was reduced to 125° C. The reaction was heated under vacuum for 6 h. during which time a yellow crystalline solid sublimed out of the reaction mixture and collected on the walls of the flask. Yield=21.7 g. Based on the structure the complex is present as the tetramer, with the crystal structure shown in FIG. 1.

Synthesis of
(n-propylcyclopentadienyl)zirconiumtrichloride

Bis(n-propylcyclopentadienyl)zirconiumdichloride (22.7 g) was heated to 130° C. with stirring forming a viscous liquid. $ZrCl_4$ (14.1 g) was added. The temperature was reduced to 125° C. The reaction was heated under vacuum for 6 h. during which time a yellow crystalline solid sublimed out of the reaction mixture and collected on the walls of the flask. Yield=21.7 g. The remaining material was again heated to 125° C. under vacuum for 6 h. resulting in an additional yield of 10.0 g. Total yield=31.7 g.

Synthesis of
n-propylcyclopentadienyl)zirconiumtrichloride
(dimethoxyethane)

Bis(n-propylcyclopentadienyl)zirconiumdichloride (13.86 g) and $ZrCl_4$ (8.68 g) were added together as solids at 120° C. and heated under vacuum for 7 h. during which time a yellow crystalline solid sublimed out of the reaction mixture and collected on the walls of the flask. Yield=19.08 g. The solid was dissolved in toluene (ca. 70 mL) and DME (ca. 25 mL) was added. This was heated to 80° C. forming a clear solution which formed a colorless crystalline solid upon cooling to room temperature. A solution of toluene and pentane (ca. 50 mL; 1 to 1 ratio) was added and the mixture was cooled to −22° C. The resulting solid was isolated by filtration, washed with pentane (2×60 mL) and dried under vacuum. Yield=23.2 g (85% yield based on bis(n-propylcyclopentadienyl)zirconiumdichloride)

Synthesis of
(n-propylcyclopentadienyl)zirconiumtrichloride
(dimethoxyethane)

Figure 2:
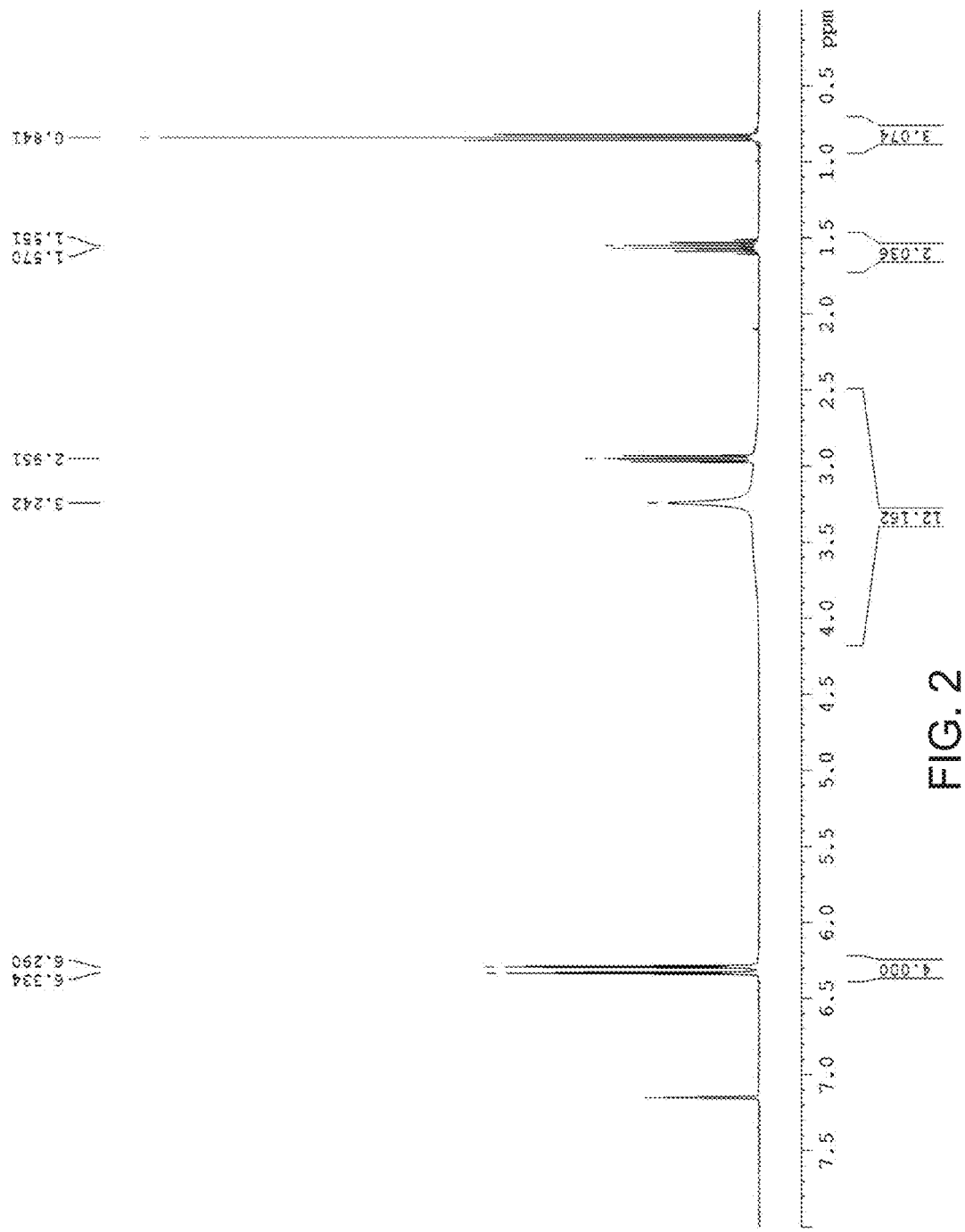
FIG. 2 is an NMR spectrum of (n-propylcyclopentadienyl)zirconiumtrichloride (dimethoxyethane).

Bis(n-propylcyclopentadienyl)zirconiumdichloride (13.25 g; 35.3 mmol) and $ZrCl_4$ (8.20 g; 35.2 mmol) were added together as solids and heated to 135° C. for 30 min resulting in a thick liquid. The reaction was heated under vacuum for 7.5 h. during which time a yellow crystalline solid sublimed out of the reaction mixture and collected on the walls of the flask. Yield=17.2 g. All the solid was dissolved in toluene (ca. 80 mL) and DME (ca 30 mL) added. The flask was heated to about 90° C. to dissolve all the solids and an aliquot was removed, dried down and the $^1$H NMR in $C_6D_6$ was taken which showed (n-propylcyclopentadienyl)zirconiumtrichloride with bis(n-propylcyclopentadienyl)zirconiumdichloride (ca. 3%) and an almost barely detectable DME peak associated with $ZrCl_4$. Upon cooling a colorless crystalline material precipitated, pentane (ca. 70 mL) was added with stirring. The solid was isolated by filtration, washed with pentane (ca. 50 mL) and dried under vacuum. Yield=19.25 g. The $^1$H NMR in $C_6D_6$ is shown in FIG. 2 and showed no detectable impurities.

Figure 3:
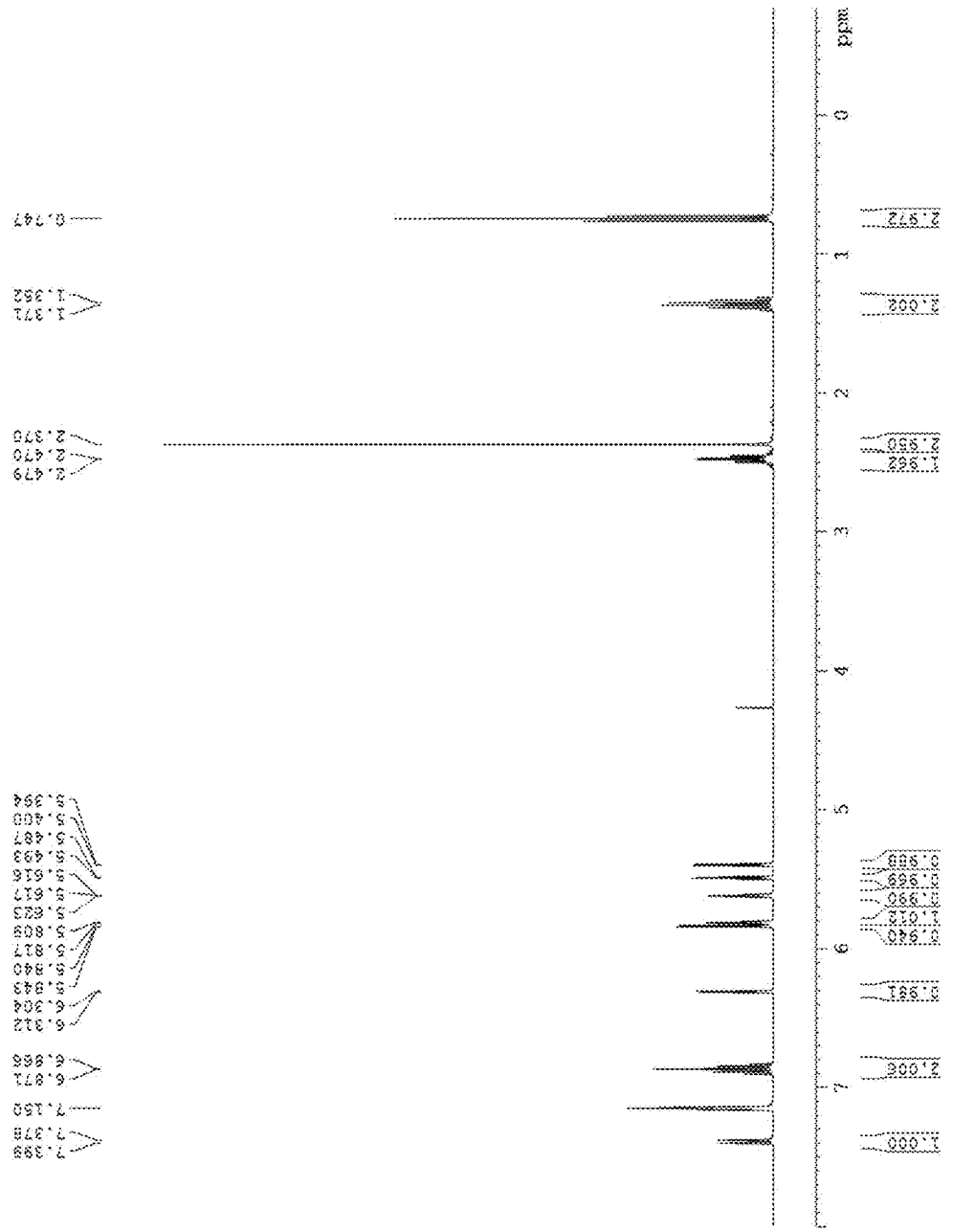
FIG. 3 is an NMR spectrum of (n-propylcyclopentadienyl)(1-methylindenyl) zirconiumdichloride.

Synthesis of
(n-propylcyclopentadienyl)(1-methylindenyl)
zirconiumdichloride 1-methylindenyllithium (8.13 g, 60 mmol)) was dissolved in 300 mL diethylether and solid (n-propylcyclopentadienyl)zirconiumtrichloride(dimethoxyethane) (23.6 g; 60 mmol) was added rapidly and an additional 100 mL diethylether was added. After stirring overnight the diethylether was removed under vacuum, and 300 mL toluene was added. The flask was heated to 60° C. and the solution was isolated by filtration. The volume was concentrated to about 100 mL and heated to 95° C. to dissolve all solids, upon cooling yellow crystalline solid formed. Hexanes (150 mL) was added, the solid was broken up with a spatula, isolated by filtration and washed with hexanes (100 mL) and dried under vacuum at 60° C. to give 19.6 g. A second crop of product was obtained by concentration and cooling of the combined supernatant and washings. It was isolated, washed and dried as described above. Total yield=21.1 g. The solids were dissolved in $CH_2Cl_2$ and an aliquot was removed, dried down and redissolved in $C_6D_6$ to obtain the $^1H$ NMR, which is shown in FIG. 3.

Synthesis of (1,3-butyl-methyl-cyclopentadienyl) zirconiumtrichloride

Bis(1,3-butyl-methyl-cyclopentadienyl)zirconiumdichloride (1.6 g) was put into a scintillation vial and heat was turned on. As the temperature reached 75° C. the $ECl_2$ began to melt and $ZrCl_4$ (0.88 g) was added. The heat was raised to 130° C. forming a brown liquid. After 30 min a drop was removed, dissolved in DME and dried down. The $^1H$ NMR in $C_6D_6$ showed a 5:1 ratio of (1,3-butyl-methyl-cyclopentadienyl)zirconiumtrichloride to bis(1,3-butyl-methyl-cyclopentadienyl) zirconiumdiichloride with a small amount of some other product. After heating an additional hour at 130° C. a drop was analyzed as described above and showed a 5.7 to 1 ratio of (1,3-butyl-methyl-cyclopentadienyl)zirconiumtrichloride to bis(1,3-butyl-methyl-cyclopentadienyl) zirconiumdichloride.

Using a sublimation apparatus, bis(1,3-butyl-methyl-cyclopentadienyl) zirconiumdichloride (10.35 g; 23.92 mmol) was heated to about 100° C. to form a liquid and $ZrCl_4$ (5.62 g; 24.12 mmol) was added. The reaction was heated at 130° C. for 1.5 h and a small sample was removed. The $^1H$ NMR of this sample was obtained in $C_6D_6$ after treatment with DME as described above and showed a 5.7 to 1 ratio of (1,3-butyl-methyl-cyclopentadienyl) zirconiumtrichloride to bis(1,3-butyl-methyl-cyclopentadienyl) zirconiumdichloride. The reaction was heated at 130° C. for 5 h. under vacuum during this time it was noticed that the yellow oil that was subliming/distilling out of the reaction mixture was running back down into the reaction mixture. From the sublimation tube, 2.2 g of a yellow oil was obtained. The $^1H$ NMR of this sample, was obtained in $C_6D_6$ after treatment with DME, and showed mono with a trace of the bis compound.

Synthesis of (1,3-butyl-methyl-cyclopentadienyl) zirconiumtrichloride

Figure 4:
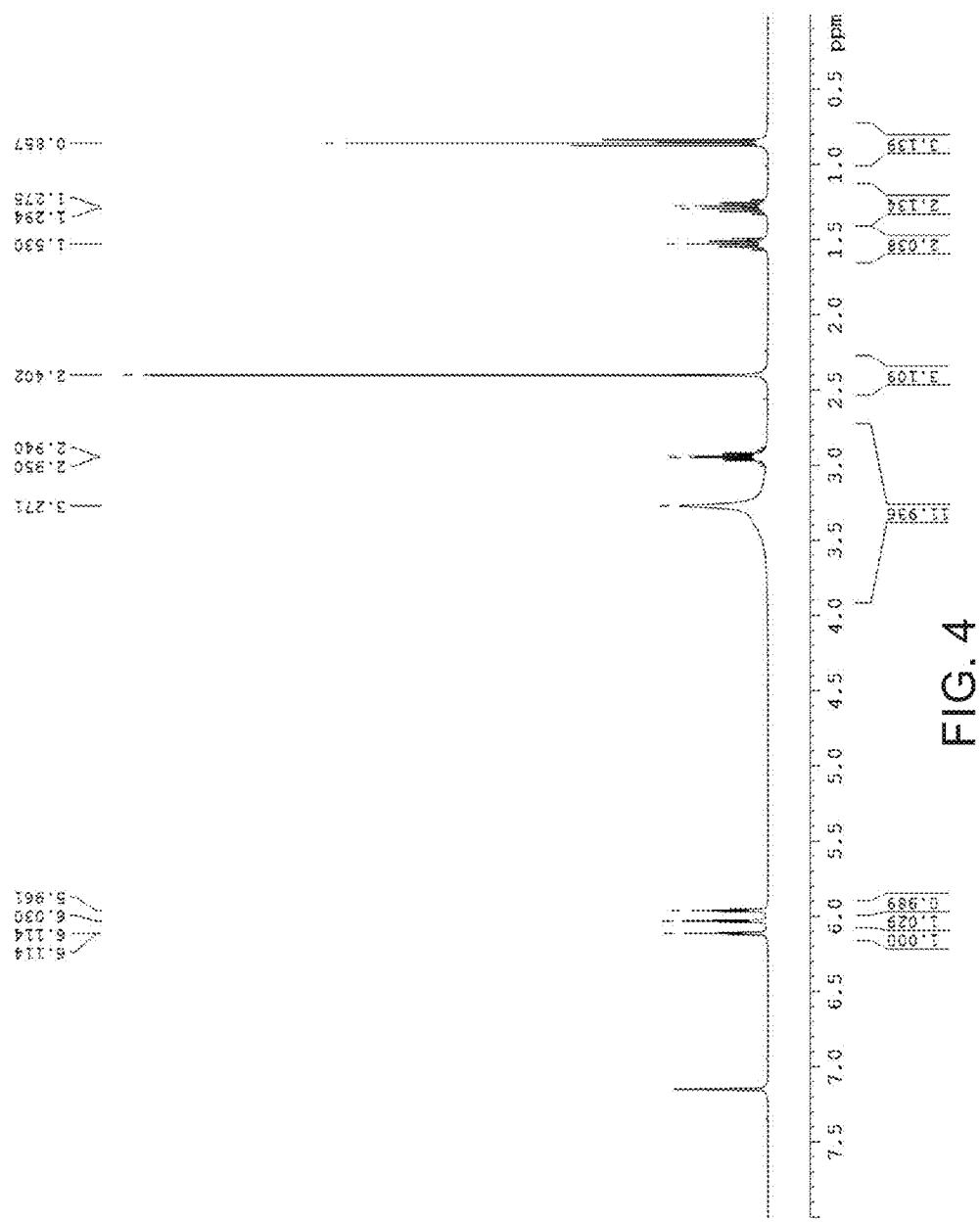
FIG. 4 is an NMR spectrum of (1,3-butyl-methyl-cyclopentadienyl) zirconiumtrichloride(dimethoxyethane).

Bis(1,3-butyl-methyl-cyclopentadienyl)zirconiumdichloride (11.12 g; 25.7 mmol) was added to a 50 mL round bottom flask and heated about 100° C. which caused it to melt. Solid $ZrCl_4$ (6.01 g; 25.7 mmol) was added. The flask was fitted to an adapter and the adapter was attached to a roto-vap bump trap and placed under vacuum. Light yellow oil collected in the trap. It was dissolved in toluene and an aliquot was removed (ca. 1 mL) treated with DME (ca. 0.5 mL) and dried down to a solid. The $^1H$ NMR in $C_6D_6$ showed the presence of (1,3-butyl-methyl-cyclopentadienyl) zirconiumtrichloride as the DME adduct (98%) and bis(1,3-butyl-methyl-cyclopentadienyl)zirconiumdichloride (2%). The toluene was removed under vacuum and the oil re-dissolved in DME (ca. 30 mL). An additional 2 g of (1,3-butyl-methyl-cyclopentadienyl)zirconiumtrichloride was dissolved in DME and added to the solution along with toluene (ca. 30 mL). The solvent was removed under vacuum leaving a light yellow oil. Pentane (ca. 50 mL) was added and the suspension was stirred vigorously. After sitting overnight the oil solidified/crystallized out. The solvent was decanted, the solid broken up, stirred with pentane (ca. 60 mL), isolated by filtration, washed with pentane (2×30 mL) and dried under vacuum to give a colorless solid. Yield=14.1 g. The $^1H$ NMR shown in FIG. 4 showed minimal impurities.

Synthesis of (n-Propylcyclopentadienyl)hafnium trichloride (dimethoxyethane)

bis(n-Propylcyclopentadienyl)hafniumdichloride [$(nPrCp)_2HfCl_2$] (25.1 g; 54.1 mmol) was heated to 140° C. in a 100 mL round-bottom flask until melted. $HfCl_4$ (17.5 g; 54.6 mmol) was added as a solid powder. The mixture was heated at 140° C. for about 30 min forming a brown viscous liquid. The 100 mL round bottom flask was attached to a short path distillation apparatus which consisted of a glass tube (90° bend) that was attached to a Schlenk flask. A vacuum was pulled on the assembly through the stopcock of the Schlenk flask. The temp was raised to 160° C. Over about an hour most of the material distilled/sublimed into the Schlenk flask or remained in the glass tube. The solid material in the u-tube was scraped out and combined with the material in the Schlenk flask. To this solid was added toluene (ca. 50 mL) and dimethoxyethane (ca. 50 mL). This was heated to reflux forming a solution, additional toluene (ca. 50 mL) was added. Upon cooling colorless needles formed. Pentane (ca. 200 mL) was added causing further formation of solid precipitate. The solid was isolated by filtration, washed with pentane (2×50 mL) and dried under vacuum. Yield=42.2 g; Cooling the combined supernatant and washings resulted an additional 2.6 g of product that was isolated. Total yield=44.8 g (86%).

Figure 5:
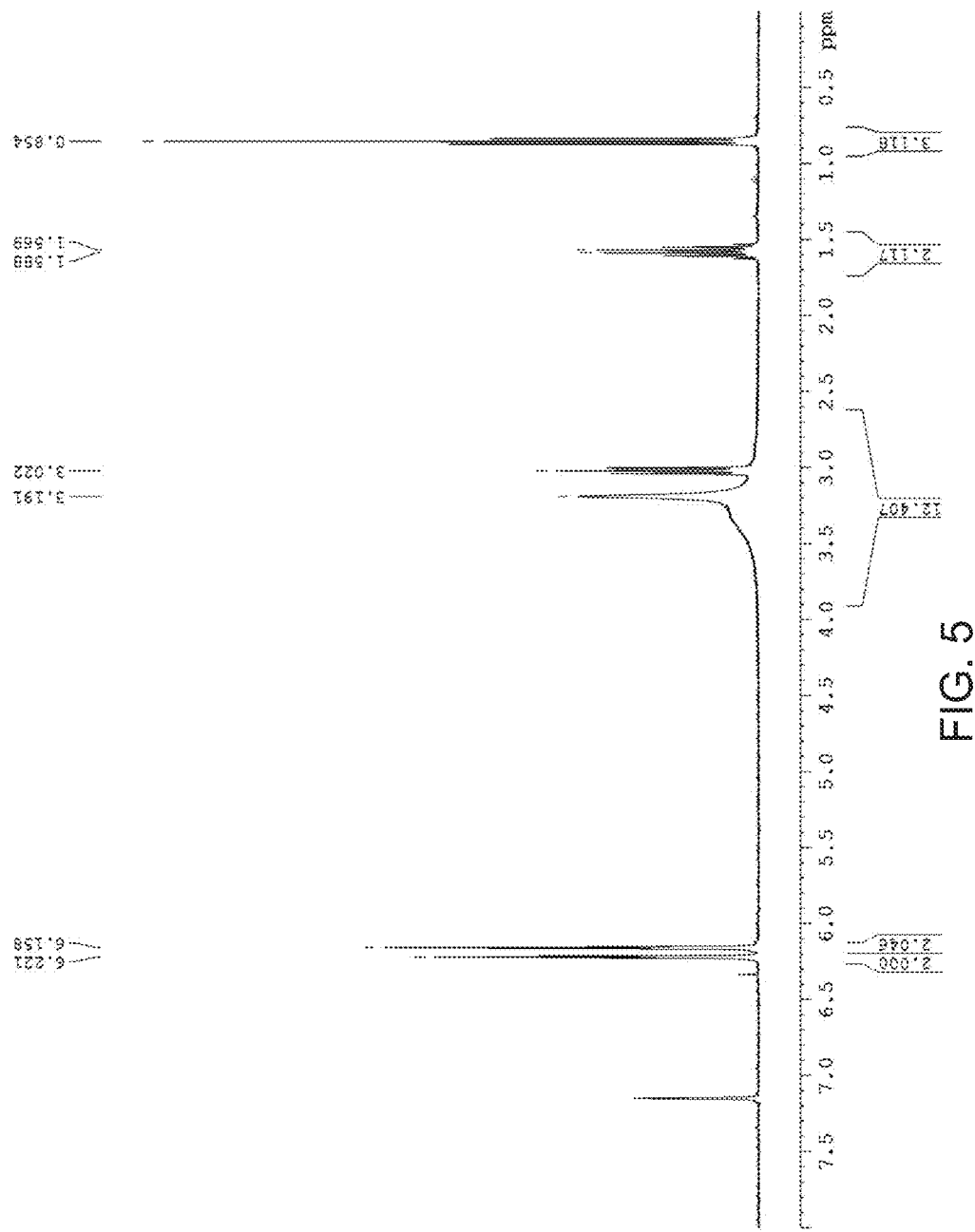
FIG. 5 is an NMR spectrum of (n-Propylcyclopentadienyl)hafnium trichloride (dimethoxyethane).

The reaction was repeated in a similar manner using 11.92 g (25.7 mmol) of $(nPrCp)_2HfCl_2$ and 8.3 g (25.9 mmol) of $HfCl_4$. The total yield of this reaction was 22.4 g (90.4%). The NMR for this compound is shown in FIG. 5.

Synthesis of a Mixed Ligand Compound

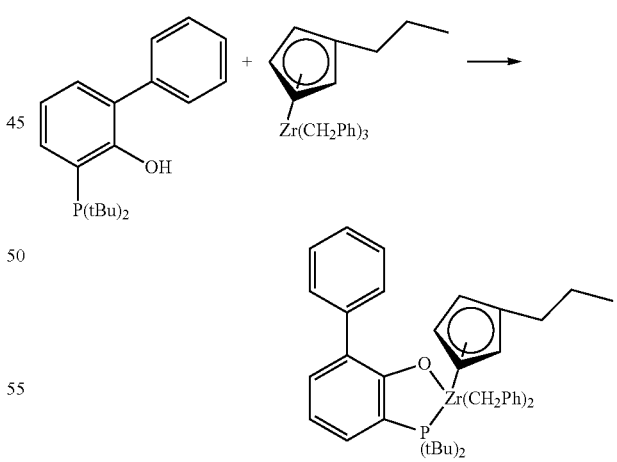

Figure 6:
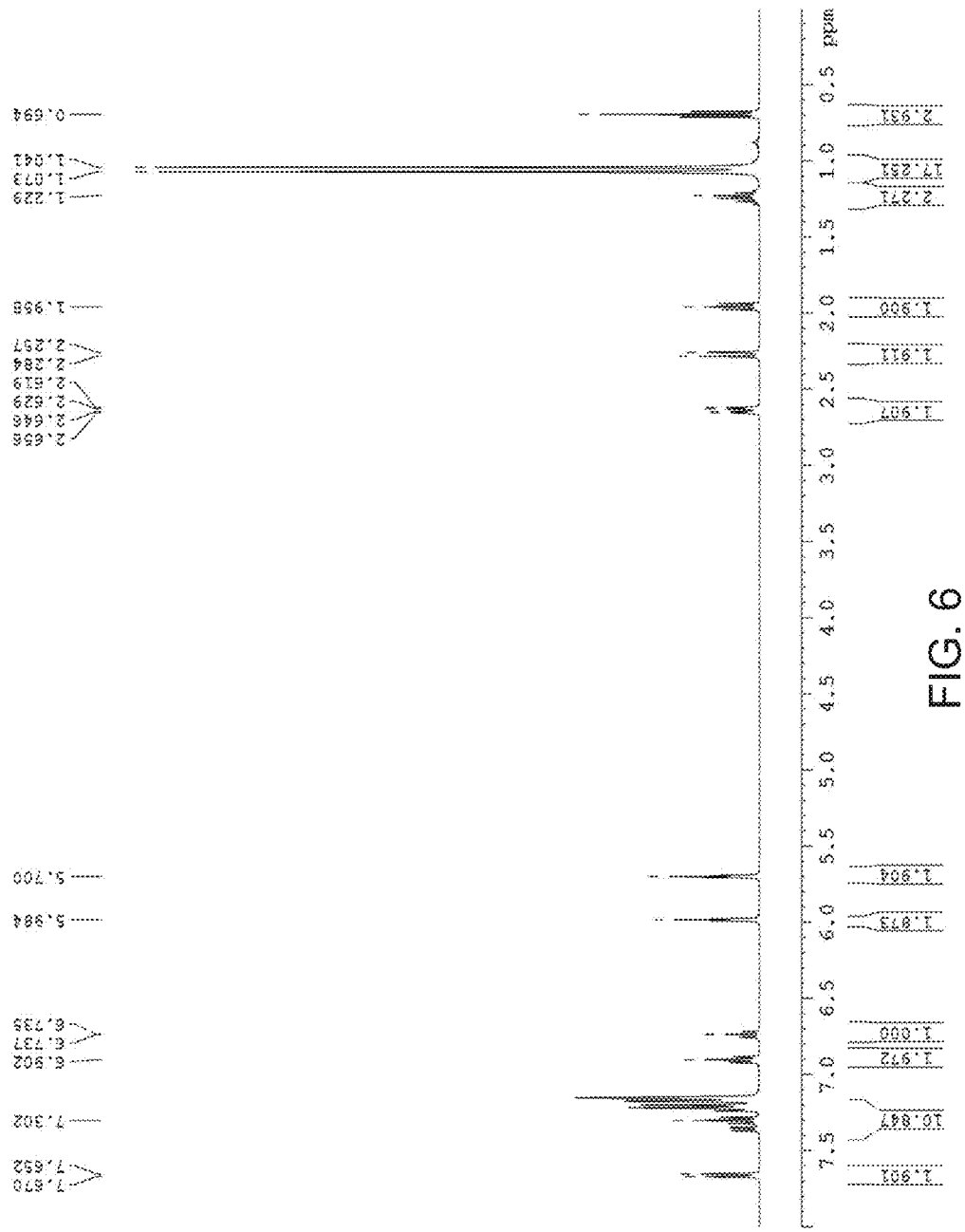
FIG. 6 is an NMR spectrum of the mixed ligand compound (nPrCp)(P,O)ZrBz$_2$.
Figure 7:
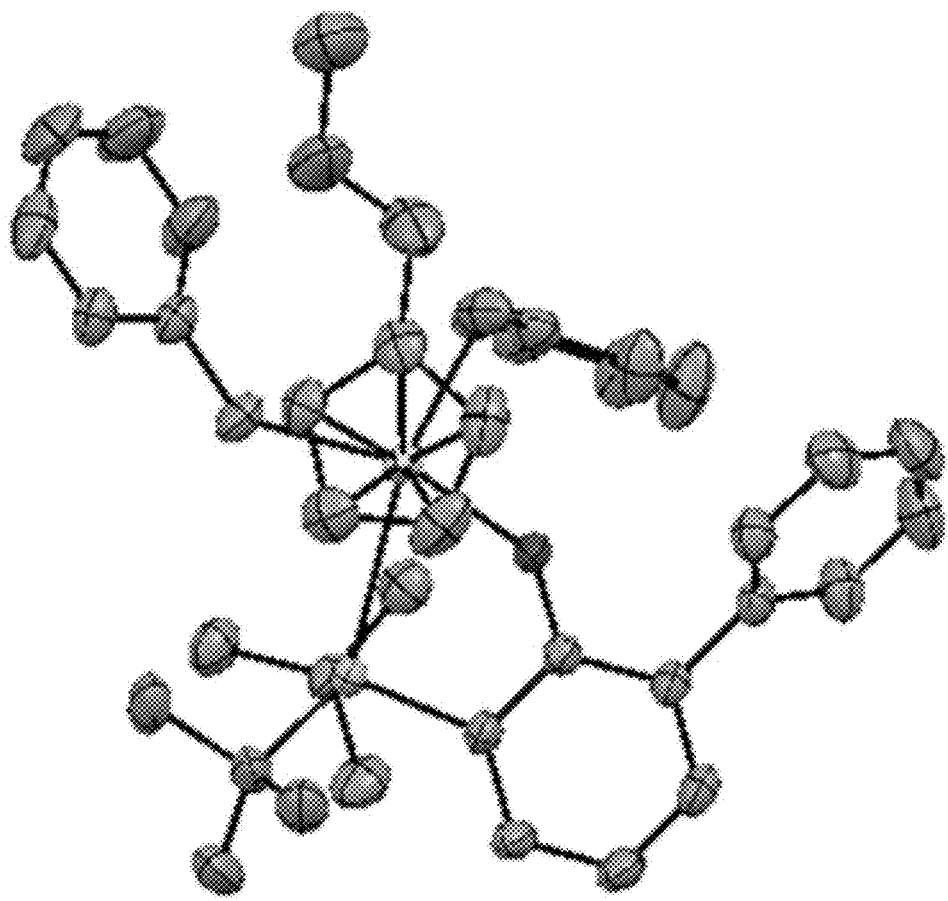
FIG. 7 is a drawing of a structure for a mixed ligand structure for using the monocyclopentadienyl complexes formed using the current techniques.

(N-propylcyclopentadienyl)zirconiumtrichloride (dimethoxyethane) (2.25 g; 5.7 mmol) was slurried in ether (50 mL) and and benzylmagnesiumchloride (1.0 M solution in ether, 19.0 mL; 19 mmol) was added. After stirring 3 h at room temperature the ether was removed under vacuum and toluene added (30 mL) forming a slurry to which 1,4-dioxane (5 mL) was added causing more precipitation to occur. The solution was isolated by filtration then dried under vacuum for 2 hours at 60° C. Yield=2.4 g. The oil was dissolved in 10.0 mL toluene to give a solution of (n-propylcyclopentadienyl)zirconiumtribenzyl with an approximate concentration of 0.194 g/mL. To 7.54 g of the (n-propylcyclopentadienyl)zirconiumtribenzyl solution (3.59 mmol of the Zr compound) was added toluene (10 mL) and a toluene solution of the phosphine ligand (solution concentration of ligand=0.138 g/mL; 7.08 g solution; 3.59 mmol of ligand). After stirring 1.5 h, the solvent was removed under vacuum and pentane was added to form a solution that was cooled at −35° C. overnight to give yellow/brown crystalline solid. The solid was isolated by decanting the supernatant and washing the solid with cold pentane. The product was recrystallized from hot hexanes to give large yellow crystals. The NMR for this compound is shown in FIG. 6. FIG. 7 is a crystal structure of this compound.

All numerical values are "about" or "approximately" the indicated value, and take into account experimental error and variations that would be expected by a person having ordinary skill in the art. Further, various terms have been defined above. To the extent a term used in a claim is not defined above, it should be given the broadest definition persons in the pertinent art have given that term as reflected in at least one printed publication or issued patent. All patents, test procedures, and other documents cited in this application are fully incorporated by reference to the extent such disclosure is not inconsistent with this application and for all jurisdictions in which such incorporation is permitted.

While the foregoing is directed to examples of the present invention, other and further examples of the invention can be devised without departing from the basic scope thereof, and the scope thereof is determined by the claims that follow.

What is claimed is:

1. A method of synthesizing a catalyst compound, comprising:

melting a dicyclopentadienyl compound comprising the following structure:

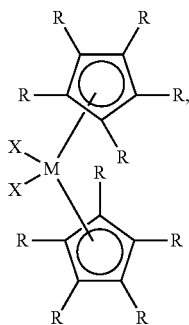

wherein M is hafnium or zirconium; each R is independently an H, a hydrocarbyl group, a substituted hydrocarbyl group, a heteroatom group; and each X is a leaving group selected from a halogen or a heteroatom group;

forming a reaction melt by adding a metal salt comprising the following structure:

depositing a monocyclopentadienyl compound from a vapor formed over the reaction melt, wherein the monocyclopentadienyl compound comprises the following structure:

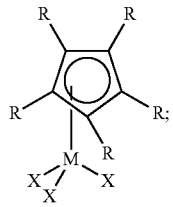

and reacting the monocyclopentadienyl compound with another ligand precursor to form the catalyst compound.

2. The method of claim 1, comprising continuously adding the dicyclopentadienyl compound and the metal salt to the reaction melt, while continuously depositing the monocyclopentadienyl compound from the vapor.

3. The method of claim 1, wherein the dicyclopentadienyl compound comprises the following structure:

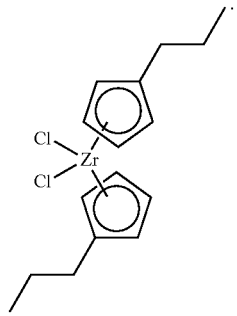

4. The method of claim 1, wherein the dicyclopentadienyl compound comprises the following structure:

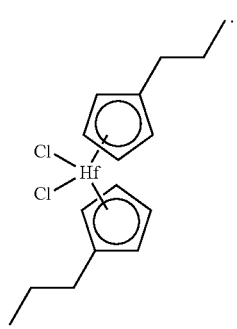

5. The method of claim 1, comprising forming a catalyst compound from the monocyclopentadienyl compound, wherein the catalyst compound comprises the formula:

$Cp^A Cp^B MX_n$, wherein $Cp^A$ is $(R_5Cp)$; and $Cp^B$ is a cyclopentadienyl, an indenyl, a tetrahydroindenyl, a fluorenyl, a substituted cyclopentadienyl, a substituted indenyl, a substituted tetrahydroindenyl, or a substituted fluorenyl.

6. The method of claim 5, wherein the catalyst compound comprises (n-propylcyclopentadienyl) (tetramethylcyclopentadienyl) zirconiumdichloride.

7. A method of forming a polyethylene copolymer comprising reacting ethylene and a $C_4$-$C_{20}$ alpha-olefin with a polymerization catalyst, wherein the polymerization catalyst is formed by:

synthesizing a monocyclopentadienyl compound comprising:

melting a dicyclopentadienyl compound comprising the following structure:

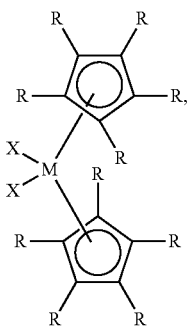

wherein M is hafnium or zirconium; each R is independently an H, a hydrocarbyl group, a substituted hydrocarbyl group, a heteroatom group; and each X is a leaving group selected from a halogen or a heteroatom group;

adding a metal salt comprising the following structure:

and depositing a monocyclopentadienyl compound from the vapor, wherein the compound comprises the following structure:

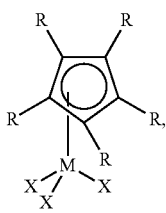

reacting the monocyclopentadienyl compound with another ligand precursor to form a catalyst compound; and activating the catalyst compound to form the polymerization catalyst.

8. The method of claim 7, wherein the dicyclopentadienyl compound comprises the following structure:

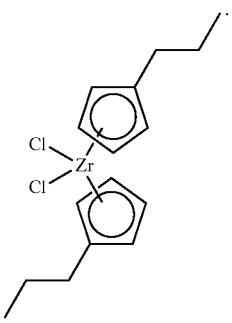

9. The method of claim 7, wherein the dicyclopentadienyl compound comprises the following structure:

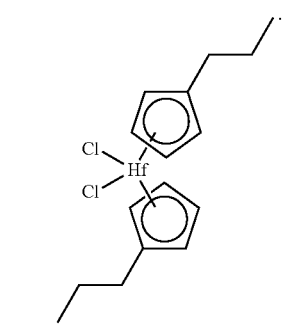

10. The method of claim 7, wherein the catalyst compound comprises the formula:

$Cp^A Cp^B MX_n$ wherein $Cp^A$ is ($R_5$-η-cyclopentadiene); and $Cp^B$ is a cyclopentadienyl, an indenyl, a tetrahydroindenyl, a fluorenyl, a substituted cyclopentadienyl, a substituted indenyl, a substituted tetrahydroindenyl, or a substituted fluorenyl.

11. The method of claim 7, comprising forming a product from the polyethylene polymer.

12. The method of claim 7, comprising combining the catalyst compound with another catalyst compound on a support to form a commonly supported catalyst system.

13. The method of claim 7, comprising:
measuring a sample of the polyethylene copolymer to obtain an initial product property; and
changing a process parameter to obtain a second product property, based, at least in part, on the initial product property.

14. The method of claim 13, wherein measuring a sample of the polyethylene copolymer comprises measuring comonomer incorporation as a function of a molecular weight.

15. The method of claim 13, wherein measuring a sample comprises determining a physical property of a polymer sample.

16. The method of claim 13, wherein measuring a sample comprises determining a flow index, a melt index, a ratio of two melt indices, a density, a molecular weight distribution, a comonomer content, or any combinations thereof.

17. The method of claim 13, wherein changing a process parameter comprises adjusting a reactor temperature.

18. The method of claim 13, wherein changing a process parameter comprises adjusting an ethylene partial pressure.

19. The method of claim 13, comprising adjusting a ratio of the comonomer to ethylene within a polymerization reactor to control a composition distribution, a molecular weight distribution, a melt index ($I_2$), or a ratio of two melt indices, or any combinations thereof, of the polyethylene copolymer.

20. The method of claim 13, comprising adjusting a ratio of hydrogen to ethylene within a polymerization reactor to control a composition distribution, a molecular weight distribution, a melt index ($I_2$), or a ratio of two melt indices, or any combinations thereof, of the polyethylene copolymer.

\* \* \* \* \*